United States Patent [19]

Taniguchi et al.

[11] Patent Number: 4,912,213

[45] Date of Patent: Mar. 27, 1990

[54] PROCESS FOR PREPARING PENICILLANIC ACID DERIVATIVES

[75] Inventors: Masatoshi Taniguchi; Michio Sasaoka; Kiyotoshi Matsumura; Ichiro Kawahara; Kenji Kase; Daisuke Suzuki, all of Tokushima; Shigeru Torii, Okayama; Hideo Tanaka, Okayama; Motoaki Tanaka, Okayama; Akira Nakai, Okayama, all of Japan

[73] Assignees: Otsuka Kagaku Kabushiki Kaisha, Osaka; Taiho Pharmaceutical Company, Limited, Tokyo, both of Japan

[21] Appl. No.: 241,186

[22] Filed: Sep. 7, 1988

[30] Foreign Application Priority Data

Sep. 7, 1987 [JP] Japan .................................. 62-224589

[51] Int. Cl.$^4$ .................. C07D 499/00; A61K 31/425
[52] U.S. Cl. .................................................... 540/310
[58] Field of Search .................. 540/310; 514/192, 195

[56] References Cited

U.S. PATENT DOCUMENTS 4,656,263  4/1987  Kellogg .............................. 540/310
4,762,920  8/1988  Carroll .............................. 540/310

Primary Examiner—Nicholas S. Rizzo

Attorney, Agent, or Firm—Birch, Stewart, Kolasch & Birch

[57] ABSTRACT

The present invention provides a process for preparing a penicillanic acid derivative of the formula

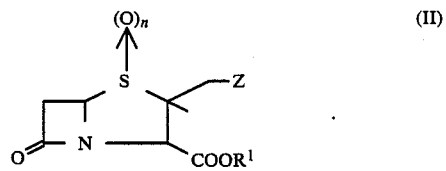

which comprises reacting lead with a halogenated penicillanic acid derivative of the formula

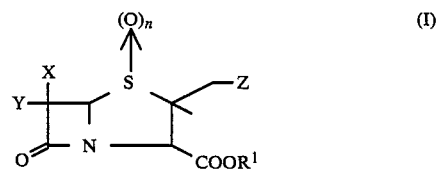

wherein X, Y, Z and $R^1$ are as defined in the specification. The reaction is advantageously conducted in the presence of a metal having higher ionization tendency than lead such as aluminum, iron, magnesium or a mixture thereof.

22 Claims, No Drawings

PROCESS FOR PREPARING PENICILLANIC ACID DERIVATIVES

The present invention relates to a novel process for preparing a penicillanic acid derivative. The penicillanic acid derivative obtained in the present invention is useful, for example, as an intermediate of β-lactamase inhibitor.

Conventionally, the following methods have been known to prepare a penicillanic acid derivative of the formula (II) from a halogenated penicillanic acid derivative of the formula (I).

A method of catalytic reduction using a noble metal catalyst, method of using tin hydride compound in an excess amount than the stoichiometric amount, method of using zinc in an excess amount than the stoichiometric amount, electrolytic reduction method, etc. [Nature, 201, 1124(1964), J. Chem. Soc., (C), 2123(1968), Japan Kokai Nos. 120588/1980, 169486/1982 and 63683/1986]. Further, a penicillanic acid 1,1-dioxide is known to be prepared with use of magnesium, but this method is not applicable to the preparation of an ester of the acid (Japan Kokai No. 120883/1985).

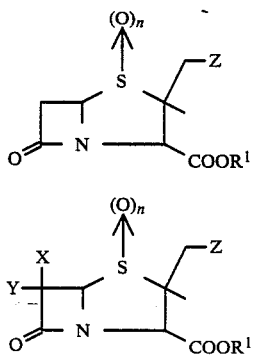

wherein X is Cl, Br or I, Y is Cl, Br, I or hydrogen atom, Z is hydrogen atom, Cl, N₃,

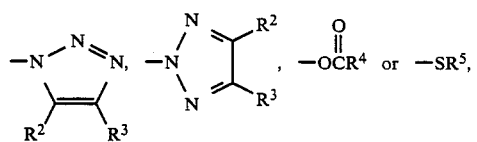

$R^1$ is a protective group of carboxylic acid, $R^2$ is hydrogen or —COOR$^4$, $R^3$ is hydrogen or —COOR$^4$, $R^4$ is lower alkyl, $R^5$ is —CN or aromatic heterocyclic ring, n is 0, 1 or 2.

The catalytic reduction method requires a large amount of an expensive noble metal catalyst and demands application of hydrogen pressure and hence is not practical. Tin hydride compound is difficult to be used industrially. The method of using zinc affords a product which is low in purity and yield. The electrolytic reduction method uses a special apparatus and produces the product in a yield of at most 75%.

An object of the invention is to provide a process for preparing a penicillanic acid derivative of the above formula (II), which is free from the above defects, safe, simple, industrially advantageous and produces the derivative in a high yield.

The above and other objects of the invention will become apparent from the following description.

The present invention provides a process for preparing a penicillanic acid derivative of the formula

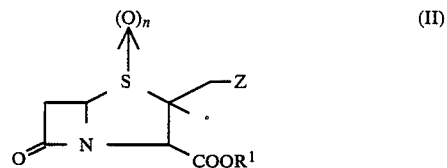

which comprises reacting lead with a halogenated penicillanic acid derivative of the formula

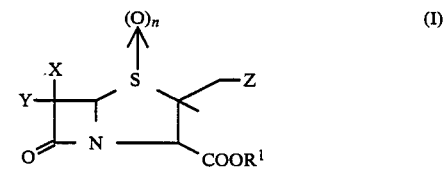

wherein X is Cl, Br or I, Y is Cl, Br, I or hydrogen atom, Z is hydrogen atom, Cl, N₃,

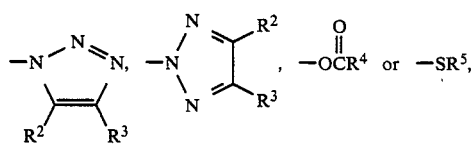

$R^1$ is a protective group of carboxylic acid, $R^2$ is hydrogen or —COOR$^4$, $R^3$ is hydrogen or —COOR$^4$, $R^4$ is lower alkyl, $R^5$ is —CN or an aromatic heterocyclic ring, n is 0, 1 or 2, and a process of the above in which a catalytic amount of lead or lead compound is used in the presence of a metal having higher ionization tendency than lead.

The present inventors have earnestly investigated to solve the above defects of the conventional methods and found that lead is an excellent reducing agent for the reaction of the present invention, although lead is seldom used as a reducing agent. Further, the pollution problem arising from the use of lead is obviated by use of a catalytic amount of lead or lead compound in the presence of a metal having higher ionization tendency than lead. Namely, in the present invention, the penicillanic acid derivative of the formula (II) is prepared in a high yield without accompanying side-products and with a simple procedure, by reacting the halogenated penicillanic acid derivative of the formula (I) with lead or a catalytic amount of lead or lead compound in the presence of a metal having a higher ionization tendency than lead in an organic solvent or aqueous organic solvent, as required with addition of an acid.

In the present invention, X is Cl, Br or I, Y is Cl, Br, I or hydrogen atom, Z is hydrogen atom, Cl, N₃,

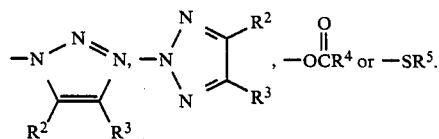

$R^2$ and $R^3$ are the same or different and are each hydrogen atom or $-COOR^4$, $R^4$ is lower alkyl. Examples of lower alkyls of $R^4$ are methyl, ethyl, propyl, i-propyl, n-butyl and t-butyl. $R^5$ is $-CN$ or aromatic heterocyclic ring. Examples of aromatic heterocyclic rings of $R^5$ are

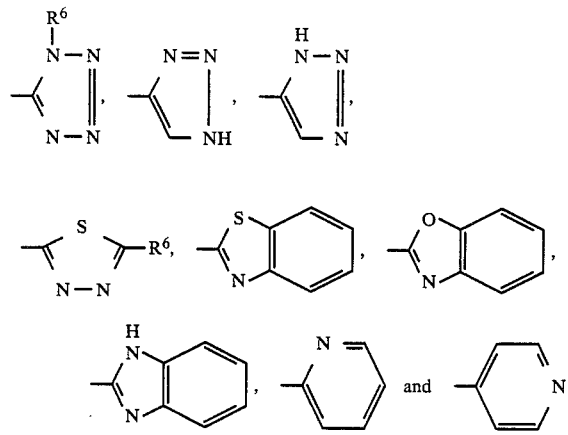

$R^6$ is methyl, ethyl, propyl, i-propyl, n-butyl, t-butyl or like lower alkyl, phenyl, $-CH_2COOH$ or $-CH_2SO_3H$.

In the present invention, $R^1$ is a protective group of carboxylic acid. Protective groups of carboxylic acid represented by $R^1$ are methyl, ethyl, propyl, isopropyl, butyl, t-butyl or like lower alkyl; methylthiomethyl, phenacyl, p-bromophenacyl, α-methylphenacyl, p-methoxyphenacyl,

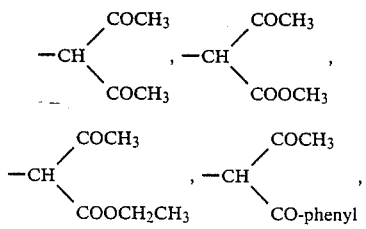

N-phthalimidomethyl or like substituted methyl; 2,2,2-trichloroethyl, 2-chloroethyl, 2-bromoethyl, 2-(trimethylsilyl)ethyl, 2-methylthioethyl, 2-(p-nitrophenylsulfenyl)ethyl, 2-(p-toluenesulfonyl)ethyl, cumyl or like substituted ethyl; cyclopentyl, cyclohexyl or like lower cycloalkyl; allyl, cinnamyl or like substituted allyl; phenyl, p-methylthiophenyl or like substituted phenyl; benzyl, triphenylmethyl, diphenylmethyl, bis(o-nitrophenyl)methyl, 9-anthrylmethyl, 2-(9,10-dioxo)-anthrylmethyl, 5-dibenzosuberyl, 2,4,6-trimethylbenzyl, p-bromobenzyl, o-nitrobenzyl, p-nitrobenzyl, p-methoxybenzyl, piperonyl, 4-picolyl or like substituted benzyl; trimethylsilyl, t-butyldimethylsilyl, triethylsilyl, i-propyldimethylsilyl, phenyldimethylsilyl or like substituted silyl. n is 0, 1 or 2.

In the present invention, the halogenated penicillanic acid derivative of the above formula (I) is reacted with a metal lead. The metal lead is not limited in shape and may be selected from a wide forms such as powder, plate, bulk, wire or needle. Powdery metal lead is preferably used in order to complete the reaction at a lower temperature in a shorter period of time. The particle size of powdery metal lead is selected from a wide range but is preferably about 10 to 500 mesh. The amount of the metal lead to be used is usually about 1.0 to 10 equivalent moles, preferably about 1.0 to 4.0 equivalent moles per halogen atom of the halogenated penicillanic acid derivative of the formula (I).

In the invention, it is possible to extremely reduce the amount of the metal lead, render the waste treatment easy and conduct the reduction at lower temperature and in shorter period, by the conjoint use of a metal or metals having higher ionization tendency than lead in the reaction system. Examples of these metals are aluminum, iron or magnesium. These metals can be used singly or in mixture of at least two of them. The metals to be used are not limited in shape and may be selected from wide forms such as powder, plate, foil, bulk, wire or needle. Powdery metal is preferably used in order to proceed the reaction smoothly. The particle size of powdery metal is selected from a wide range but is preferably about 10 to 300 mesh. The amount of the metal to be used having higher ionization tendency than lead is usually about 1.0 to 50 equivalent moles, preferably about 1.0 to 5.0 equivalent moles per halogen atom of the halogenated penicillanic acid derivative of the formula (I).

In case of using the metal having higher ionization tendency than lead, it is possible to use a lead compound in place of metal lead.

The above lead compound may be one containing lead having a valency of zero, two or four. Further, these compounds may be in the form of a hydrate. As the lead compound, conventionally known compounds are widely used. Examples thereof are lead fluoride, lead chloride, lead bromide, lead iodide or like lead halide, lead nitrate, lead sulfate, lead perchlorate, lead borate, lead carbonate, lead phosphate or like lead salt of inorganic acid, lead acetate, lead oxalate, lead stearate or like lead salt of aliphatic acid, lead oxide, lead hydroxide, or chelates of lead having a valency of zero, 2 or 4. Examples of ligands for the chelate are ethylenediamine tetraacetic acid, nitrilotriacetic acid or like chelating agent, ketone, ester, carboxylic acid, amine, oxime, ammonia, nitrile, organic phosphine or like compounds which coordinate with oxygen, nitrogen or phosphorus atom. These lead compounds can be used singly or in mixture of at least two of them. Although only one atom of lead or one molecule of lead compound is theoretically required, the amount thereof to be used is usually about 0.00001 to 0.5 equivalent mole, preferably about 0.0001 to 0.2 equivalent mole per halogen atom of the starting halogenated penicillanic acid derivative of the formula (I).

The present reduction reaction is conducted in an organic solvent, in aqueous organic solvent, or in two phase system of water and water-insoluble organic solvent, when required with addition of an acid. Organic solvents are selected from a wide range of compounds which dissolve the compound of the formula (I) and are inert in the reaction condition. Examples thereof are methanol, ethanol, propanol, isopropanol, butanol, tert-butanol or like alcohol; methyl formate, ethyl formate, propyl formate, butyl formate, methyl acetate, ethyl acetate, propyl acetate, butyl acetate, methyl propionate, ethyl propionate or like lower alkyl esters of lower aliphatic acids; acetone, methyl ethyl ketone, methyl propyl ketone, methyl butyl ketone, methyl isobutyl ketone, diethyl ketone or like ketones; diethyl ether, ethyl propyl ether, ethyl butyl ether, dipropyl ether, diisopropyl ether, dibutyl ether, methyl cellosolve, dimethoxyethane or like ethers; tetrahydrofuran, dioxane or like cyclic ethers; acetonitrile, propionitrile, butyronitrile, isobutyronitrile, valeronitrile or like nitriles; benzene, toluene, xylene, chlorobenzene, anisole or like substituted or unsubstituted aromatic hydrocarbons; dichloromethane, chloroform, dichloroethane, trichloroethane, dibromoethane, propylene-dichloride, carbon tetrachloride, freons or like halogenated hydrocarbons; pentane, hexane, heptane, octane or like hydrocarbons; cyclopentane, cyclohexane, cycloheptane, cyclooctane or like cycloalkanes; dimethyl formamide, dimethyl acetamide or like amides; and dimethyl sulfoxide. These solvents can be used singly or in mixture of at least two of them, and may contain water as required. The amount of the solvent is usually about 0.5 to 200 l, preferably about 1 to 50 l per kg of the compound of the formula (I).

As an acid used as required in the invention are inorganic acids and organic acids ranging from strong acid to weak acid. Examples thereof are hydrochloric acid, sulfuric acid, nitric acid, perchloric acid, hydrobromic acid, hydroiodic acid, hydrofluoric acid, bromous acid, bromic acid, hypochlorous acid, hypobromous acid, phosphoric acid, phosphorous acid, boric acid, silicic acid or like mineral acid, formic acid, acetic acid, propionic acid, oxalic acid, tartaric acid, benzoic acid, malic acid, malonic acid, monochloroacetic acid, dichloroacetic acid, trichloroacetic acid, trifluoroacetic acid or like carboxylic acid, benzenesulfonic acid, toluenesulfonic acid, naphthalenesulfonic acid, methanesulfonic acid, trifluoromethanesulfonic acid, chlorosulfonic acid or like sulfonic acid, benzenesulfinic acid, toluenesulfinic acid or like sulfinic acid, ascorbic acid, Meldrum's acid, Squaric acid, pyromeconic acid, lower alkyl ester of malonic acid, lower alkyl ester of acetoacetic acid, phenol, cresol, barbituric acid or like acidic compound, etc., or a salt of the acid wherein an aqueous solution of the salt is acidic.

The reaction temperature depends on the kinds of the starting material, solvent, etc., but is usually about −20° C. to 150° C., preferably about 0° C. to 70° C. The present reaction sometimes proceeds more rapidly when conducted with irradiation of ultrasonic waves. After completion of the reaction, the reaction mixture is for example extracted to obtain the desired penicillanic acid derivative of the formula (II) in almost pure form. Further, the derivative can be purified as required by recrystallization, column chromatography or like usual means.

The present invention has the following advantages by finding lead is an excellent reducing agent.
1. The penicillanic acid derivative can be prepared in extremely high selectivity and yield without requiring a further purification.
2. The present desired compound can be prepared with use of easily available equipment and with a simple procedure without a special apparatus.
3. Generally, strict limitations are demanded in view of public pollution for conducting a reaction which uses a heavy metal as a reagent on an industrial scale. In the present invention, it is possible to reduce the amount of lead or lead compound to an extremely small amount by conjoint use of a metal which has no pollution problem, and to make easy the treatment of the reaction waste.

As stated above, the present invention provides an extremely advantageous method in industrial scale for preparing a penicillanic acid derivative.

The present invention will be described in greater detail with reference to the following examples.

EXAMPLE 1

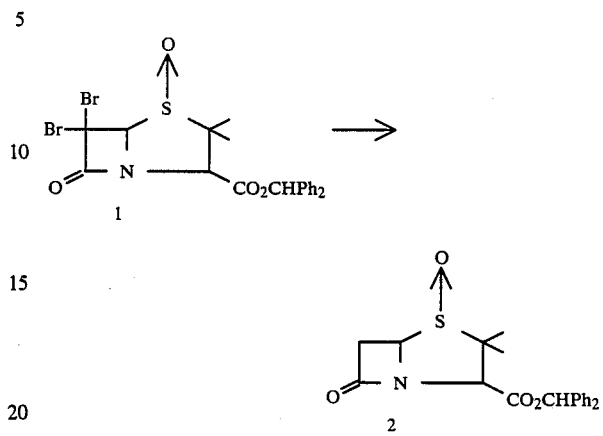

In 4 ml of tetrahydrofuran was dissolved Compound 1 (1080 mg). Thereto was added a solution of 353 mg of $NH_4Cl$ in 1 ml of water. To the mixture were added 162 mg of aluminum powder, 56 mg of $PbCl_2$ and 19 mg of malic acid and reacted with stirring. The reaction was continued at 20° to 30° C. of the inner temperature for 2 hours with cooling because the reaction was exothermic. After completion of the reaction, tetrahydrofuran was removed by a rotary evaporator. To the resulting concentrate was added dichloromethane and the insolubles were filtered off with use of celite. The filtrate was allowed to place. The separated dichloromethane layer was dried over anhydrous $MgSO_4$ and concentrated at a reduced pressure to obtain Compound 2 in a yield of 90%. The NMR spectra were well consistent with the structure. In the above formulae, Ph is phenyl.

NMR($CDCl_3$, δ ppm): 1.11(3H, s), 1.57(3H, s), 3.34(1H, dd, J=2 Hz, 17 Hz), 3.50(1H, dd, J=4 Hz, 17 Hz), 4.48(1H, s), 4.53(1H, dd, J=2 Hz, 4 Hz), 6.93(1H, s), 7.32(10H, bs)

EXAMPLE 2

In 4 ml of dichloromethane was dissolved Compound 1 (1000 mg). Thereto was added a solution of 350 mg of $NH_4Cl$ in 1 ml of water. To the mixture were added 160 mg of aluminum powder and 10 mg of lead powder and reacted with stirring. The reaction was continued at 20° to 30° C. of the inner temperature for 1.5 hours. After completion of the reaction, the mixture was allowed to place. The separated dichloromethane layer was dried over anhydrous $MgSO_4$ and concentrated at a reduced pressure to obtain Compound 2 in a yield of 92%. The NMR spectra were well consistent with the structure.

EXAMPLE 3

In 40 ml of dichloromethane was dissolved Compound 1 (10.8 g). Thereto was added a solution of 2.4 g of $NH_4Cl$ in 10 ml of water. To the mixture were added 1.2 g of aluminum powder and 0.1 g of $PbCl_2$ and reacted with stirring. The reaction was continued at 20° to 30° C. of the inner temperature for 2 hours. After completion of the reaction, the mixture was allowed to place. The separated dichloromethane layer was dried over anhydrous $MgSO_4$ and concentrated at a reduced pressure to obtain Compound 2 in a yield of 95%. The NMR spectra were well consistent with the structure.

EXAMPLE 4

Compound 2 was prepared from Compound 1 in the same manner as in Example 1 except that acetone was used in place of tetrahydrofuran.

EXAMPLE 5

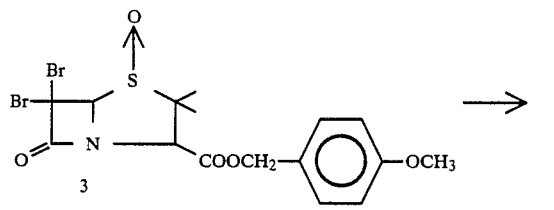

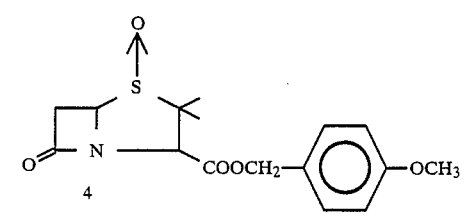

In 0.9 ml of methanol was dissolved Compound 3 (99 mg). Thereto was added 0.1 ml of 1% of hydrobromic acid. To the mixture were added 12 mg of finely cut aluminum foil and 7.2 mg of $PbBr_2$ and the mixture was reacted at room temperature with stirring. Upon consumption of all aluminum foil, 2 ml of 1N-HCl wwas added to the reaction mixture and the mixture was extracted with 5 ml of ethyl acetate. The ethyl acetate layer was washed with saturated aqueous solution of each of sodium hydrogencarbonate and sodium chloride, dried over anhydrous sodium sulfate and concentrated at a reduced pressure to obtain Compound 4 in a yield of 92%. The NMR spectra were well consistent with the structure.

NMR(CDCl$_3$, δ ppm): 1.25(3H, s), 1.54(3H, s), 3.35(1H, dd, J=2 Hz, 17 Hz), 3.53(1H, dd, J=4 Hz, 17 Hz), 3.80(3H, s), 4.35(1H, sH), 4.55(1H, dd, J=2 Hz, 4 Hz), 5.10 and 5.15(2H, ABq, J=12 Hz), 6.87(2H, d, J=10 Hz), 7.28(2H, d, J=10 Hz)

EXAMPLE 6

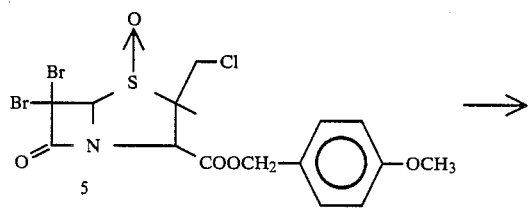

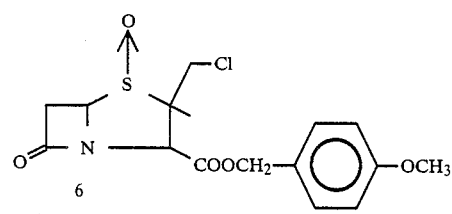

In a solvent mixture of 1 ml of dichloromethane and 0.8 ml of methanol was dissolved Compound 5 (201 mg). Thereto was added 0.2 ml of 1% of hydrobromic acid. To the mixture were added 23.4 mg of finely cut aluminum foil and 14.3 mg of $PbCl_2$ and the mixture was reacted at room temperature with stirring. Upon consumption of all of aluminum foil, 2 ml of 1N-HCl was added to the reaction mixture and the mixture was extracted with 20 ml of ethyl acetate. The ethyl acetate layer was washed with saturated aqueous solution of each of sodium hydrogencarbonate and sodium chloride, dried over anhydrous sodium sulfate and concentrated at a reduced pressure to obtain Compound 6 in a yield of 90%. The NMR spectra were well consistent with the structure.

NMR(CDCl$_3$, δ ppm): 1.22(3H, s), 3.22(1H, dd, J=2 Hz, 17 Hz), 3.58(1H, dd, J=4 Hz, 17 Hz), 3.74(5H, s), 4.51(1H, dd, J=2 Hz, 4 Hz), 4.70(1H, s), 4.98 and 5.20(2H, ABq, J=11 Hz), 6.79(2H, d, J=8 Hz), 7.23(2H, d, J=8 Hz)

EXAMPLE 7

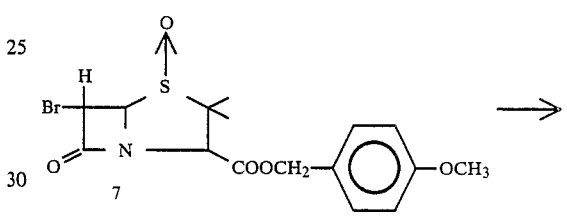

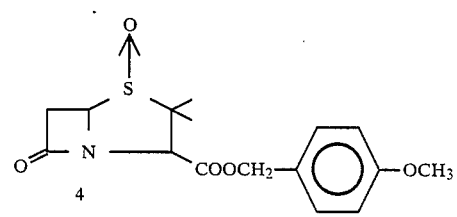

Compound 4 was obtained in a yield of 90% in the same manner as in Example 5 with the exception of using Compound 7 as a starting material.

EXAMPLES 8 TO 15

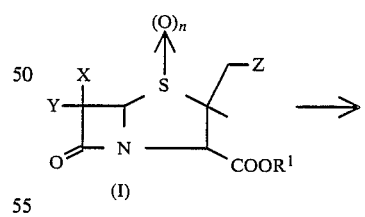

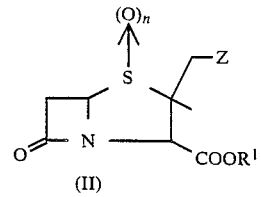

The reactions were conducted in the same manner as in Example 5 with use of Compound (I) listed in Table 1. Products (II) listed in Table 1 were obtained in high yields and selectivities.

TABLE 1

| | Starting material (I) | | | | | Product (II) | | |
|---|---|---|---|---|---|---|---|---|
| Ex. | X | Y | n | Z | $R^1$ | n | Z | $R^1$ |
| 8 | H | Br | 0 | −N(N=N triazole ring) | −CHPh$_2$ | 0 | −N(N=N triazole ring) | −CHPh$_2$ |
| 9 | " | " | " | " | −CH$_2$−C$_6$H$_4$−OCH$_3$ | " | " | −CH$_2$−C$_6$H$_4$−OCH$_3$ |
| 10 | " | " | " | −SCN | −CHPh$_2$ | " | −SCN | −CHPh$_2$ |
| 11 | " | " | " | −OC(O)CH$_3$ | " | " | −OC(O)CH$_3$ | " |
| 12 | " | " | " | N$_3$ | " | " | N$_3$ | " |
| 13 | " | " | " | −S−(methyltetrazole) | " | " | −S−(methyltetrazole) | " |
| 14 | " | I | " | H | " | " | H | " |
| 15 | Br | Br | 2 | " | −CH$_2$−C$_6$H$_4$−OCH$_3$ | 2 | " | −CH$_2$−C$_6$H$_4$−OCH$_3$ |

We claim:
1. A process for preparing a penicillanic acid derivative of the formula

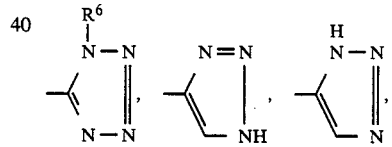

which comprises reacting an effective amount of lead with a halogenated penicillanic acid derivtive of the formula

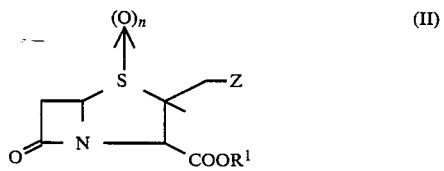

wherein X is Cl, Br or I, Y is Cl, Br, I or a hydrogen atom, Z is a hydrogen atom, Cl, N$_3$,

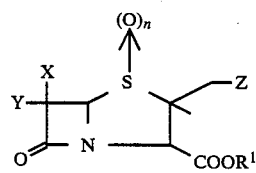

or −SR$^5$, R$^1$ is a protective group of carboxylic acid, R$^2$ is hydrogen or −COOR$^4$, R$^3$ is hydrogen or −COOR$^4$, R$^4$ is lower alkyl, R$^5$ is −CN or an aromatic heterocyclic ring selected from the group consisting of

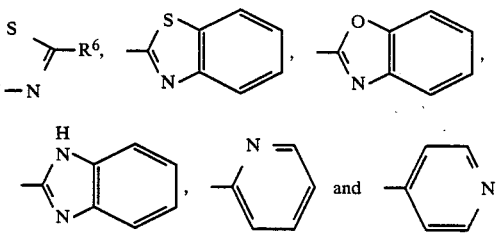

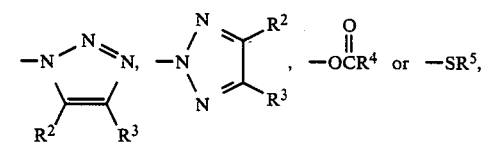

where R$^6$ is lower alkyl, phenyl, −CH$_2$COOH or CH$_2$SO$_3$H and n is 0, 1 or 2.

2. The process of claim 1, wherein the amount of lead is 1.0 to 10 equivalent moles per halogen atom of the halogenated penicillanic acid derivative of the formula (I).

3. The process of claim 2, wherein the reaction is conducted in an organic solvent, an aqueous organic solvent or in a two-phase system of water and a water-insoluble organic solvent.

4. The process of claim 1, which is conducted at a temperature of −20° to 150° C.

5. A process for preparing a penicillanic acid derivative of the formula

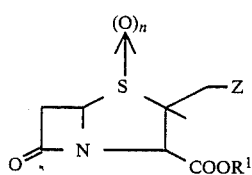

which comprises reacting a catalytic amount of lead or lead compound with a halogenated penicillanic acid derivative of the formula

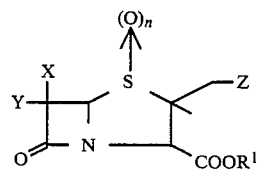

wherein X is Cl, Br or I, Y is Cl, Br, I or a hydrogen atom, Z is a hydrogen atom, Cl, $N_3$,

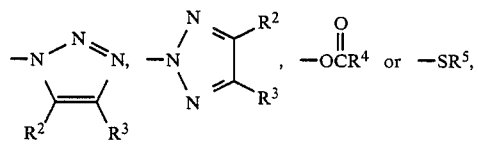

or $-SR^5$, $R^1$ is a protective group of carboxylic acid, $R^2$ is hydrogen or $-COOR^4$, $R^3$ is hydrogen or $-COOR^4$, $R^4$ is lower alkyl, $R^5$ is $-CN$ or an aromatic heterocyclic ring selected from the group consisting of

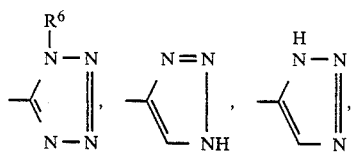

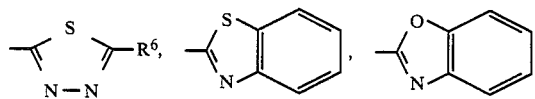

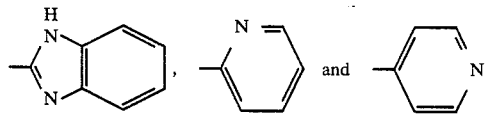

where $R^6$ is lower alkyl, phenyl, $-CH_2COOH$ or $CH_2SO_3H$ and n is 0, 1 or 2, in the presence of a metal having a higher ionization tendency than lead selected from the group consisting of aluminum, iron, magnesium or a mixture thereof.

6. The process of claim 5, wherein the metal having higher ionization tendency than lead is aluminum.

7. A process for preparing a penicillanic acid derivative of the formula

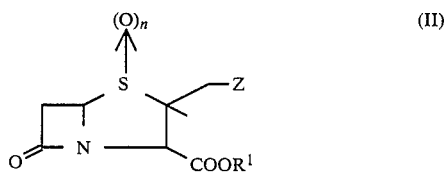

which consists essentially of:
reacting lead or a lead compound selected from the group consisting of a lead salt of an inorganic acid, a lead salt of an aliphatic acid, lead oxide, lead hydroxide and chelates of lead having a valency of 0, 2 or 4 with a halogenated penicillanic acid derivative of the formula

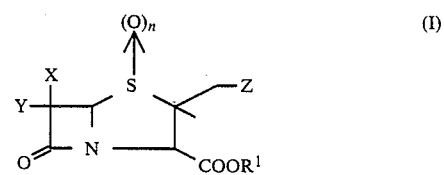

wherein X is Cl, Br or I, Y is Cl, Br, I or a hydrogen atom, Z is a hydrogen atom, Cl, $N_3$,

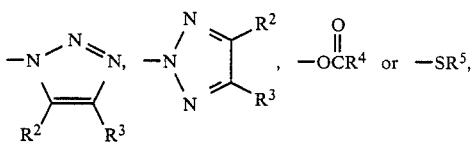

or $-SR^5$, $R^1$ is a protective group of carboxylic acid, $R^2$ is hydrogen or $-COOR^4$, $R^3$ is hydrogen or $-COOR^4$, $R^4$ is lower alkyl, $R^5$ is $-CN$ or an aromatic heterocyclic ring selected from the group consisting of

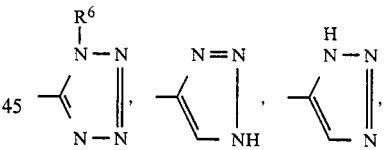

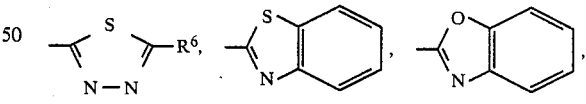

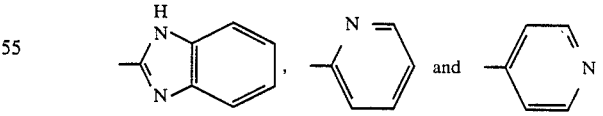

wherein $R^6$ is lower alkyl, phenyl, $-CH_2COOH$ or $CH_2SO_3H$ and n is 0, 1 or 2 in a solvent which dissolves said compound of the formula (I) and which is insert under the reaction conditions, at a temperature of $-20°$ C. to 150° C. wherein the amount of lead or lead compound is about 0.00001 to 0.5 equivalent moles per halogen atom of the halogenated penicillanic acid derivative of the formula (I) and in the presence of a metal having a higher ionization tendency than lead selected from the group consisting of aluminum, iron, magnesium or a mixture thereof in an amount of 1.0 to 50 equivalent moles per halogen atom of the halogenated penicillanic acid of the formula (I).

8. The process of claim 1, 5 or 7, wherein said protective group of carboxylic acid is selected from the group consisting of a lower alkyl group, a substituted methyl group, a substituted ethyl group, a cycloalkyl group, an allyl group, a substituted allyl group, a phenyl group, a substituted phenyl group, a benzyl group, a substituted benzyl group and a substituted silyl group.

9. The process of claim 7, wherein said lead or lead compound is powdery metal lead.

10. The process of claim 7, wherein said solvent is selected from the group consisting of an alcohol, a lower alkyl ester of a lower aliphatic acid, a ketone, an ether, a cyclic ether, a nitrile, a substituted or unsubstituted aromatic hydrocarbon, a halogenated hydrocarbon, a hydrocarbon, a cycloalkane, an amide and dimethylsulfoxide.

11. The process of claim 7, wherein the amount of said solvent is 0.5 to 200 liters per kg of the compound of the formula (I).

12. The process of claim 7, wherein the amount of said solvent is 1 to 50 liters per kg of the compound of the formula (I).

13. The process of claim 7, wherein the reaction is conducted in an organic solvent, an aqueous organic solvent or in a two-phase system of water and a water-insoluble organic solvent.

14. The process of claim 1, 5 or 7, which is conducted in the presence of an acid.

15. The process of claim 1, which is conducted in the presence of an acid selected from the group consisting of mineral acid, carboxylic acid, sulfonic acid, sulfinic acid, ascorbic acid, Meldrum's acid, Squaric acid, pyromeconic acid, lower alkyl ester of malonic acid, lower alkyl ester of acetoacetic acid, phenol, cresol, barbituric acid or a salt of any of said acids in which an aqueous solution of said salt is acidic.

16. The process of claim 7, which is conducted at a temperature of 0° to 70° C.

17. The process of claim 7, which further comprises extracting said penicillanic acid derivative of the formula (II) in almost pure form.

18. The process of claim 1, 5 or 7, wherein X and Y are both independently selected from the group consisting of Cl, Br or I.

19. The process of claim 11, wherein X and Y are both the same.

20. The process of claim 1, wherein said halogenated penicillanic acid derivative of the formula (I) is

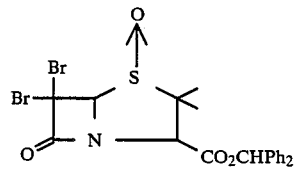

and wherein said penicillanic acid derivative of the formula (II) is

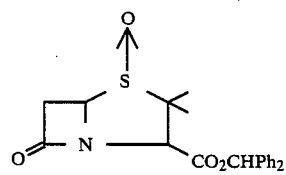

21. The process of claim 1, wherein X and Y are both Br and n is 1.

22. The process of claim 21, wherein Z is hydrogen.

* * * * *